United States Patent

Honarpour et al.

[11] Patent Number: 5,493,226
[45] Date of Patent: Feb. 20, 1996

[54] METHOD AND APPARATUS FOR MEASURING PROPERTIES OF CORE SAMPLES INCLUDING HEATING AND PRESSURIZING THE CORE SAMPLE AND MEASURING THE DYNAMIC AND STATIC CAPILLARY PRESSURE OF WATER IN THE CORE SAMPLE

[75] Inventors: Mehdi M. Honarpour, High Village; Da-Teh D. Huang, Plano; David W. Payton, Carrollton; Ralph Navarro, Dallas, all of Tex.

[73] Assignee: Mobile Oil Corporation, Fairfax, Va.

[21] Appl. No.: 224,920

[22] Filed: Apr. 8, 1994

[51] Int. Cl.[6] .............................. G01V 3/06; E21B 41/02
[52] U.S. Cl. .................................. 324/376; 73/153
[58] Field of Search .................................. 324/376, 639, 324/640, 641; 73/38, 153; 250/253, 255

[56] References Cited

U.S. PATENT DOCUMENTS

| | | | |
|---|---|---|---|
| 3,617,868 | 11/1971 | Beitel | 324/376 |
| 4,486,714 | 12/1984 | Davis, Jr. et al. | 324/376 |
| 4,506,542 | 3/1985 | Rose | 73/38 |
| 4,543,821 | 10/1985 | Davis, Jr. | 73/38 |
| 4,807,448 | 3/1990 | Givens | 324/376 |
| 4,924,187 | 5/1990 | Sprunt et al. | 324/376 |
| 4,926,128 | 5/1990 | Givens | 324/376 |
| 5,079,948 | 1/1992 | Collins et al. | 73/38 |
| 5,095,273 | 3/1992 | Kennedy et al. | 324/376 |
| 5,209,104 | 5/1993 | Collins et al. | 324/376 |
| 5,297,420 | 3/1994 | Gilliland et al. | 73/38 |
| 5,341,101 | 8/1994 | Maerefat et al. | 324/376 |

*Primary Examiner*—Sandra L. O'Shea
*Assistant Examiner*—Roger Phillips
*Attorney, Agent, or Firm*—Alexander J. McKillop; George W. Hager, Jr.

[57] ABSTRACT

A method and apparatus for obtaining data for simultaneously measuring relative permeability ($k_r$), static capillary pressure, dynamic capillary pressure ($P_c$), and electrical resistivity ($R_t$) of a core sample taken from a subterranean reservoir under simulated reservoir temperature and pressure. A core sample having a a simulated original water and oil saturation is waterflooded while (1) pressures at spaced points along the core are measured to determine $k_r$, (2) capillary pressures of the oil and water are measured to determine $P_c$; and (3) $R_t$ is measured between points spaced on the core. At the same time, the core is scanned by microwaves to determine the water saturation existing in the core at the time a particular measurement is made.

17 Claims, 6 Drawing Sheets

METHOD AND APPARATUS FOR MEASURING PROPERTIES OF CORE SAMPLES INCLUDING HEATING AND PRESSURIZING THE CORE SAMPLE AND MEASURING THE DYNAMIC AND STATIC CAPILLARY PRESSURE OF WATER IN THE CORE SAMPLE

DESCRIPTION

1. Technical Field

The present invention relates to a method and apparatus for measuring certain parameters of a core sample and in one of its aspects relates to a method and apparatus for simultaneously measuring the relative permeability, capillary pressure, and electrical resistivity of a reservoir core sample over a wide range of water saturations while maintaining the core at simulated reservoir conditions.

2. Background Art

In the production of minerals, e.g. hydrocarbons, from a subterranean reservoir, certain lithological or petrophysical properties of the reservoir are routinely determined as an aid in improving and/or maximizing production from the reservoir. Among the more important of these properties are those which are commonly known as "relative permeability", "capillary pressure", and "electrical resistivity". There are several different known techniques available for making these measurements but each of these techniques is likely to yield a measurement which may be substantially different from the same measurement taken by a different technique. For example, (a) measurements of residual fluid saturations routinely vary depending on how the measurements are made; (b) the direction of saturation change is likely to be different in different experiments; and (c) measurements of preferential wettability may change from one experiment to another due to the required handling, repeated testing, and/or core restoration.

As a further example of how measurements may vary, there are two basic methods for measuring relative permeability of a core sample; i.e. the steady-state method and the dynamic displacement method. In each method, a cylindrical core sample is saturated with water/brine and is then oil-flooded to a residual water saturation. Subsequently, the core is water-flooded and the pressure drop across the core is measured along with the oil and water production. The average saturations within the core are determined from the overall material balance. When the steady-state method is used, lengthy measurement times are necessitated because fluid flow must be stabilized within the core before each measurement. The dynamic displacement method, while overcoming this problem, suffers from capillary end effects whereby it is generally effective only for high flow rates.

When using either method for measuring relative permeability, an accurate measurement of fluid saturation in the core is required; i.e. desired accuracy within 2%. Currently, there are both external and in situ techniques known for determining the fluid saturation of a core sample where external techniques (e.g. material balance) are used, the saturations in the core are inferred indirectly by measuring fluid production. While this provides an average value, it does not reveal information as to the saturation profile within the core. Further, due to fluid separation and evaporation losses, significant errors may occur during steady-state, material balance measurements when the core volume is small. Recirculating systems have been used with material balance equipment to aid in reducing these errors.

Gravimetric and extraction methods are other external techniques commonly used to determine water saturation in a core. In the gravimetric method, the core is weighed before and during the test and the saturation is inferred from the change in weight. In the extraction method, fluid saturation is determined using distillation/extraction. Both of these methods require removal of the core sample from the core holder which may cause pressure cycling, wettability alteration, and saturation changes which, in turn, can lead to errors in the final measurements.

In situ techniques allow fluid saturation measurements to be made inside the core directly without disruption. The measurements taken by these techniques are generally considered more accurate and reliable than those taken by external techniques. Examples of such situ techniques include the use of gamma-ray and multidimensional computerized tomography (CT); see U.S. Pat. Nos. 4,157,472 to Beck et al; 4,283,629 to Habermehl; 4,399,509 to Hounsfield; 4,422,177 to Mastronardi et al; 4,649,483 to Dixon; and 4,868,751 to Dogru. However, finding a safe and suitable tagging agent to use in these techniques is sometimes difficult because the tagging agent may not mix well with the injection/produced fluids and may interact adversely with the rock matrix of the core sample. Another potential problem in using these techniques lies in the mass transfer between fluids that changes tagging fluid concentration which, in turn, may result in erroneous saturation measurement.

Still another in situ technique involves the use of microwave-attenuation wherein a microwave-sending horn and a receiving horn are positioned on opposite sides of a core. The sending horn focuses microwave radiation into and through the core to the receiving horn. The detected or received signals are processed through a logarithmic amplifier to produce a voltage which, in turn, is proportional to the saturation in the core at that point. The horns are mounted on a trolley or the like so they can move across the core and take a position-verses-saturation "snapshot" at a plurality of predetermined points across the core. For a more complete description of such a technique, see: (a) "Microwave Attention-A New Tool for Monitoring Saturations in Laboratory Flooding Experiments", R. W. Parsons, (SPE 4985), Houston, Tex., Oct. 6–9, 1974; (b) "Microwave Spectroscopic Analysis of Surfactant/Polymer Flooding", D. T. Wasan et al, (SPE 8327) Las Vegas, , Nev. Sep. 23–26, 1979; (c) "Effect of Fractional Flow Hysteresis on Recovery of Tertiary Oil" R. E. Gladfelter et al, SOCIETY OF PETROLEUM ENGINEERS JOURNAL, pps. 508–520, December, 1980; and (d) "Determination of Oil Saturation Distributions in Field Cores By Microwave Spectroscopy", D. F. Brost et al, (SPE 10110), San Antonio, Tex., Oct. 5–7, 1981.

While providing a point-by-point profile of the water saturation in a scanned core, the measurements are made at basically ambient conditions which do not correspond to the original reservoir conditions which, in turn, may have a substantial effect on the accuracy of the final measurements.

Electrical resistivity is still another known method for determining brine saturation within a core. However, this method only provides average saturations between electrodes. Inaccuracies in these measurements at low brine saturations often occur because of the discontinuity of flow channels and the high noise of the electrodes.

Capillary pressure ($P_c$) measurements may be conventionally obtained by a variety of different methods, e.g. porous plate, centrifuge, or mercury injection methods. The data from these methods are obtained either under static conditions (i.e. porous plate and mercury injection) or gravity-dominated conditions (i.e. centrifuge), each of which give rise to certain problems. For example, it is difficult to measure $P_c$ over a complete cycle using the porous plate method; it is impossible to measure negative $P_c$ (in the imbibition direction) using the mercury injection method; and while a complete cycle of drainage-imbibition $P_c$ can be obtained using the centrifuge method, this method skips the spontaneous imbibition and drainage process and only provides information in the forced imbibition and drainage directions.

Further, as will be understood by those skilled in this art, relative permeability and capillary pressure are interrelated and should be measured simultaneously. However, these properties are commonly obtained from different measurements using different methods, fluids, and testing conditions on different core samples from the same reservoir. As can be imagined, this results in inconsistencies between the collected data. For example, the residual oil and brine saturation values obtained from relative permeability measurements often differ substantially from those derived from capillary pressure measurements. Further, these properties have to be measured over a narrow range of saturation changes in the core sample because of a lack of flexibility in achieving low values of residual fluid saturations.

To alleviate these problems, methods have been proposed for measuring both the relative permeability and the capillary pressure based on the flow of two fluid phases through a core sample; see (a) "A New Technique to Measure Static and Dynamic Properties of a Partially Saturated Porous Medium", T. S. Ramakrishnan et al, CHEMICAL ENGINEERING SCIENCE, Vol. 46, No. 4, pp. 1157–1163 1991, and (b) "Dynamic Capillary Pressure Curve for Water/Oil Displacement in Porous Media", F. J-M. Kalaydijian, (SPE 24813), Washington, D.C., Oct. 4–7, 1992.

As can be seen from the above discussions, significant efforts have been made in developing techniques for measuring the various properties of a core sample. However, a need still exists for the ability to make these measurements simultaneously on the same core sample while that core is being maintained at conditions (e.g. temperatures and pressures) which simulate those of the original reservoir from which the core was obtained.

SUMMARY OF THE INVENTION

The present invention provides a method and apparatus for obtaining data for simultaneously measuring relative permeability ($k_r$), dynamic capillary pressure ($P_c$), and electrical resistivity ($R_t$) of a core sample taken from a subterranean reservoir. Further, static capillary pressure of the core can be established and a highly accurate, water-saturation profile in the core sample can be measured at any time.

In carrying out the present method, water is injected into a core sample from a subterranean reservoir until the core is substantially 100% water-saturated. The core sample is then desaturated by flowing a hydrocarbon fluid (i.e. oil and/or gas) therethrough until the residual water saturation is substantially equal to that which simulates the original water saturation of the reservoir from which the core sample was taken. Either before or after the desired saturation is established in the core sample, elevated temperature and pressure are applied to the core to thereby simulate the original temperature and pressure of the reservoir after which the core sample is flooded with a drive fluid, e.g. water/brine, to simulate a recovery operation.

Before and during the flooding of the core, the core sample is scanned at spaced points with microwave signals to determine the water saturation of said core sample at each of said spaced points. Also, while the core is being flooded, the pressure in core sample is measured at points spaced along the core with these pressure measurements being used to determine the relative permeability of the core. At the same time, the dynamic capillary pressures of both the water and the hydrocarbon fluid in said core sample are measured to arrive at the dynamic capillary pressure of the core sample. Simultaneously with the measuring of the various pressures in the core, the electrical resistivity of said core sample is also measured between spaced point along said core sample.

The apparatus in accordance with the present invention is comprised of a cabinet or oven which is capable of being heated to high temperatures (e.g. up to about 200° F.). A compartment or bath is fluidly connected to the oven whereby circulated, heated air from the oven will establish the same, high temperatures in the bath. A core holder is positioned within said bath and has a body which is adapted to receive the core sample. An elastic sleeve, e.g. rubber, is adapted to fit tightly around said core sample and is positioned with the core sample into the core holder.

A recirculating pump system is provided for individually injecting both water and the hydrocarbon fluid into the core sample in the core holder and for collecting and recirculating all fluids which exit from the core after they pass therethrough. The pump system is housed in the oven so that all of the fluids being pumped will be heated to the desired temperature before passing through the core sample.

A microwave scanning system forms part of the apparatus and is used for scanning the core sample at a plurality of spaced points along the core holder to determine the water saturation of said core sample at that point at the time a particular scan is made. The microwave system is comprised of a sending horn for transmitting microwave signals through said core sample at each of the spaced point and a receiving horn for receiving those signals after they have passed through said core sample. The horns are positioned on the outside of said bath so that they lie on opposite sides of the core sample. The horns are mounted on a yoke or the like which is moved along the core in precise increments during the scanning operation. The amount of attenuation of particular signals caused by water molecules in the core can be used to calculate the water saturation at that point.

Both the bath and the body of said core holder are made of microwave transparent material so that the microwave signals will pass therethrough with little or no attenuation. Likewise, the elastic sleeve has diametrically-opposed slots therein which are adapted to align with said microwave horns when said sleeve is properly positioned in the core holder. Microwave-absorbent material, e.g. foam, is positioned between the sleeve and the body of the core holder when the sleeve and the core sample are in the core holder to absorb any microwaves which do not pass through the core. The microwave-absorbent material has windows therein which align with said slots in said sleeve to allow the microwave signals to pass through the core without any significant attenuation.

The body of the core holder around the sleeve is filled with a non-compressible fluid, e.g. oil, which, in turn, saturates the microwave-absorbent material in the body. When a desired pressure is applied to this non-compressible fluid, an elevated pressure (e.g. simulated reservoir pressure) is applied onto the core sample within the sleeve. The sleeve, in turn, has a plurality of ports spaced along its length which are adapted to be connected to pressure transducers. Pressures are measured during the flooding of the core at these spaced intervals to thereby obtain the data necessary for determining the relative permeability of the core.

At the same time, the dynamic capillary pressure of both the water and the hydrocarbon fluids are separately measured through respective openings in said sleeve and this data is used to determine the dynamic capillary pressure of the core sample. Simultaneously with these measurements, the electrical resistivity between spaced contact on the core is continuously measured during the flood operation.

BRIEF DESCRIPTION OF THE DRAWINGS

The actual construction, operation, and apparent advantages of the present invention will be better understood by referring to the drawings in which like numerals identify like parts and in which.

BEST KNOWN MODE FOR CARRYING OUT THE INVENTION

Figure 1:
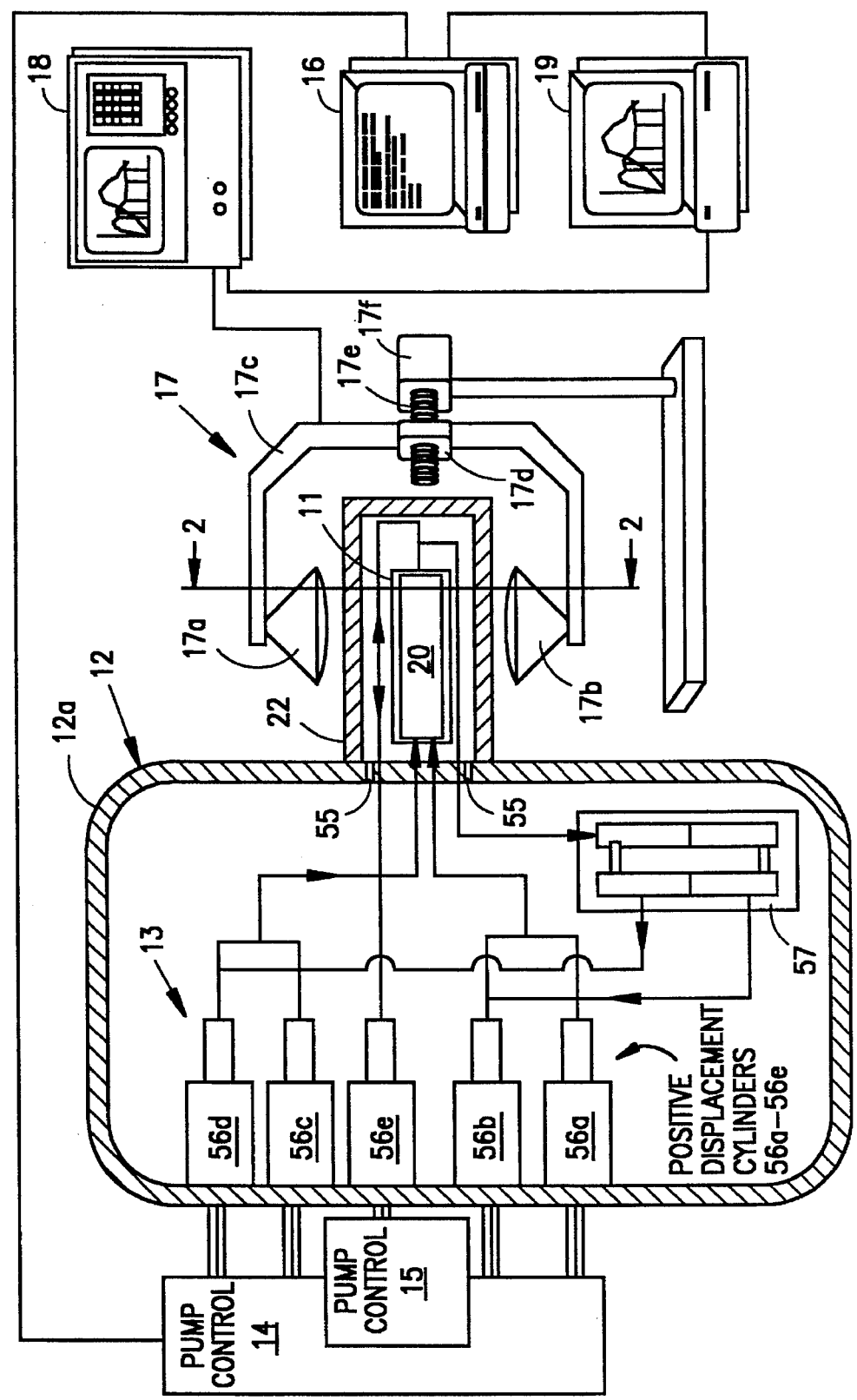
FIG. 1 is a schematical view, partly in perspective, of the apparatus in accordance with the present invention for use in measuring certain properties of a core sample.

Referring more particularly to the drawings, FIG. 1 discloses an apparatus in accordance with the present invention which has the capability both of (a) establishing a wide range of different initial water saturations in a core sample to thereby simulate various reservoir saturations in the core; and ( b ) obtaining data for simultaneously measuring relative permeability ($k_r$) , both static and dynamic capillary pressure ($P_c$), and electrical resistivity ($R_t$) while, at the same time, monitoring the in situ water saturation in the core and maintaining the core under simulated, original reservoir temperature and pressure.

More specifically, FIG. 1 discloses apparatus 10 which basically is comprised of the following integrated components: core holder 11, heating cabinet or oven 12, recirculating pump system 13, pump control system 14, 15, 16, microwave scanning system 17, microwave analyzer 18, and a computer(s) 19 or the like both for automating the operation carried out by the apparatus and for logging and analizing the data as it is collected by apparatus 10.

Referring now more specifically to the components of apparatus 10, core holder 11 is capable of providing data for simultaneously measuring $k_r$, $P_c$, and $R_t$ of a core 20 while the core is being maintained at simulated reservoir temperatures and pressures (e.g. up to about 200° F. and 5000 psi). Core holder 11 is triaxial which means the pressure can be applied both radially and axially on a core 20.

Figure 5:
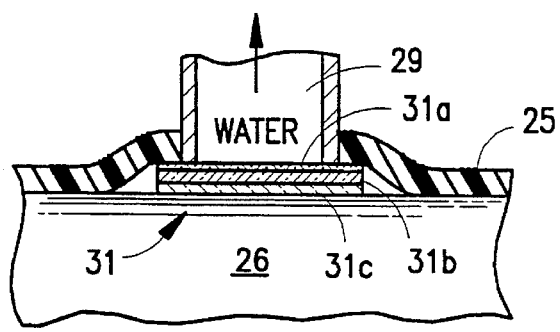
FIG. 5 is an enlarged, partly exaggerated, broken-away, sectional view of the portion of core holder showing the ports used for measuring capillary pressure of a core sample.
Figure 5:
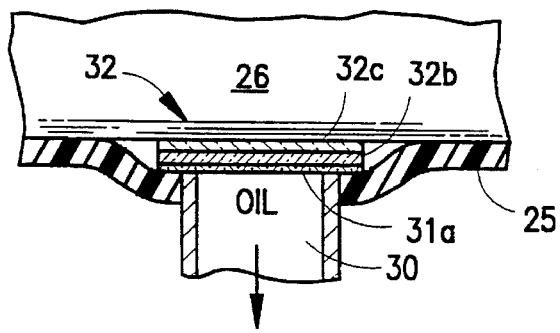
Figure 2:
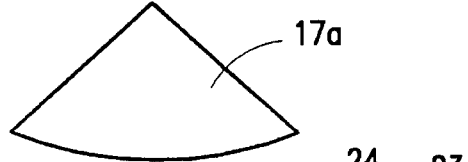
FIG. 2 is an enlarged sectional view of the core holder taken along line 2—2 of FIG. 1 with certain elements not shown for the sake of clarity.
Figure 2:
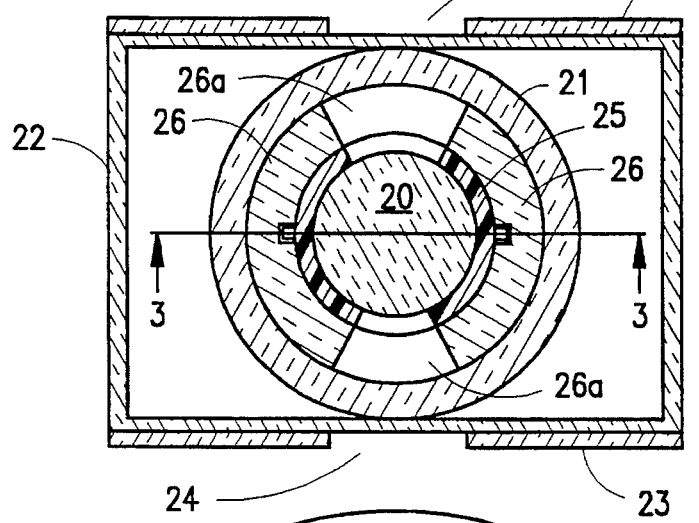
Figure 2:
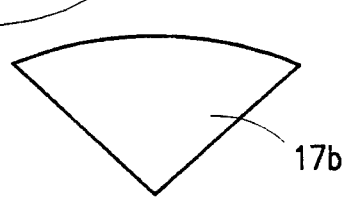

As can better be seen from FIGS. 2 and 5, core holder 11 comprises body 21 (e.g. 8" diameter, 14" long) which is positioned within housing or bath 22 which, in turn, is an extension or compartment of heating cabinet 12, as will be more fully explained later. Both body 21 and bath 22 are made of a nonmetallic composite, fiberglass-reinforced, microwave compatable material (e.g. S-2 fiberglass and epoxy resin). Bath 22 has a covering layer of microwave-absorbent material 23 (e.g. Ecosorb LS-28 foam, Emerson & Cumings, Canton, Mass.) on the top and bottom thereof, each of which, in turn, has a respective window 24 (2" by 6") provided therein for a purpose to be described later.

An inner elastic sleeve 25 (e.g. Viton 70D rubber or the like) snuggly fits over core sample 20 (e.g. 2" diameter, 6" long) and is positioned therewith into core holder body 21. Sleeve 25 and core 20 are held in position by microwave absorbent material 26 (e.g.Ecosorb LS-26 foam, Emerson & Cumings, Canton, Mass.) which, in turn, has upper and lower openings 26$a$therethrough to align with windows 24.

Figure 3:
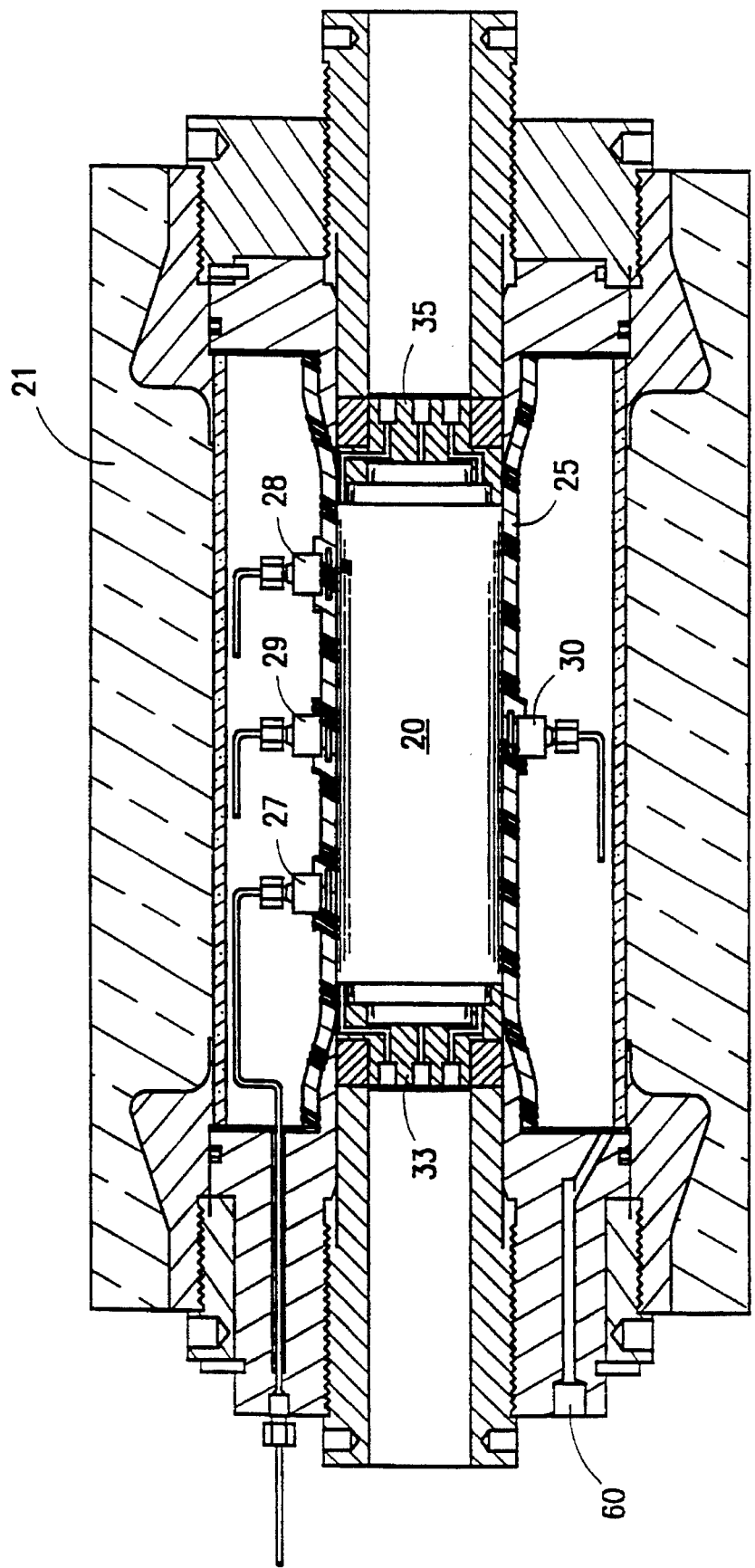
FIG. 3 is a sectional view of the core holder taken along line 3—3 of FIG. 2.
Figure 4:
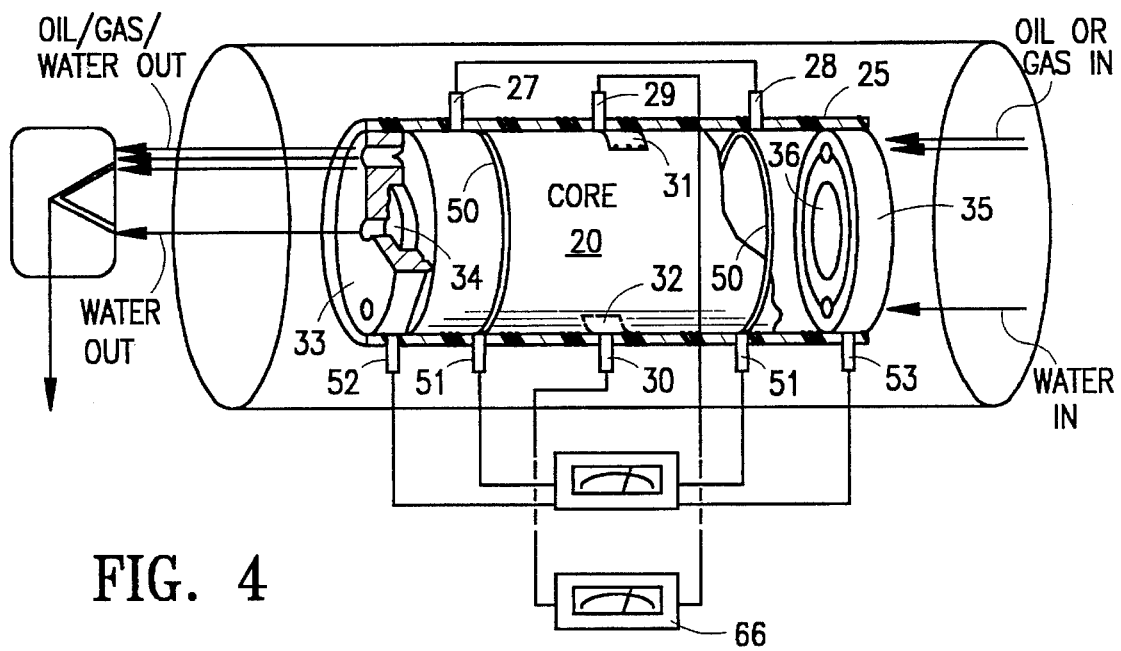
FIG. 4 is a schematical view, partly in perspective, as the core holder of shown in FIG. 3.

As shown in FIGS. 3 and 4, sleeve 25 has openings for four (4) pressure ports or openings 27–30. Ports 27, 28 are spaced from each other along the longitudinal axis of the sleeve (e.g. 5" apart) and are adapted to be connected to pressure transducers or the like (not shown) to provide pressure measurements which, in turn, are used to calculate the relative permeability of the core 20, as will be further discussed below. It should be understood that additional ports can be spaced along the sleeve 25 to provide additional pressure measurements, if desired.

Ports 29, 30 are adapted to measure the pressures of oil and water, respectively, to thereby provide measurements for calculating the dynamic capillary pressure of the core. As shown, ports 29, 30 are located on opposite sides of sleeve 25 near the midpoint of the sleeve. However, the exact placement of these ports are not critical. Referring now to FIGS. 4 and 5, patches 31, 32 or the like are positioned onto core 20 at predetermined locations wherein patches 31, 32 will align with their respective openings or ports 29, 30 when core 20 is properly positioned within sleeve 25. Basically, each patch functions to allow only its respective fluid (i.e. water or oil) to pass therethrough.

More specifically, patch 31 is preferably formed of thin screen layer 31$a$, a water-wet membrane 31$b$ (e.g. cellose with smaller than 0.1 micron pore-throat size equivalent to 100 Bar bubble pressure such as distributed by Soil Moisture Co. Santa Barbara, Calif.), and a water-wet cushioning paper 31$c$ (e.g.Whatman #1filter paper, Whatman International Ltd, Maidstone, England). Likewise, patch 32 is formed of screen layer 32a, oil-wet membrane 32b (e.g. polypropylene with 45 psi bubble pressure), and an oil cushion paper layer 32c. As will be understood in the art, only water will pass through patch 31 while only oil will pass through patch 32 for a purpose to be described below.

Ceramic porous plates are provided in endpieces 33, 35 which hold core 20 within core holder 11. Endpiece 33 includes a water-wet porous plate 34 while endpiece 35 includes an oil-wet porous plate 36. These plates are used to provide the flexibility in establishing the residual fluids saturations and also to allow the measurements required for the static capillary pressure calculations. Even though each plate allows a different fluid to flow therethrough, both endpieces are similar in construction so only one will be described in detail.

Figure 6:
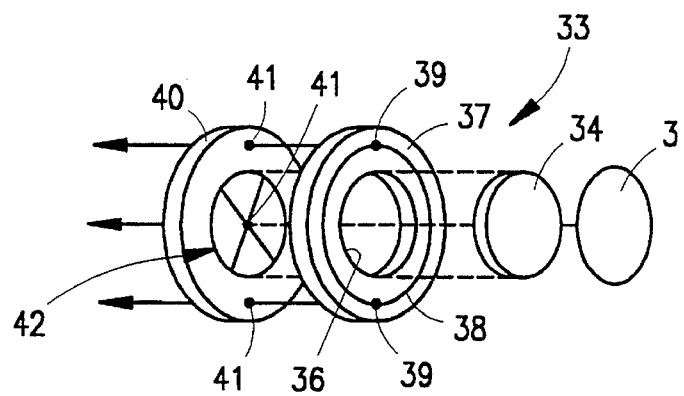
FIG. 6 is an exploded view of an endpiece for the core holder of FIG. 2.

Referring to FIG. 6, a typical endpiece 33 is comprised of a membrane 34a (i.e. one with a high bubble pressure) which covers water-wet, ceramic porous plate 34 which, in turn, is carried in opening 36 in ring 37. Ring 37 has a fluid-distributing, circumferential groove 38 and two fluid by-pass openings 39 therein. Ring 37 and plate 34 are held in position by end plate 40 which, in turn, has three fluid inlet/outlet openings 41 therethrough. End plate 40 also has a pattern of grooves 42 to distribute/collect fluid(s) as it flows therethrough.

Also positioned on core 20 are electrically-conductive bands 50 (FIG. 4) which are spaced along the longitudinal axis thereof so that they will be aligned with respective contacts 51 on sleeve 25 when core 20 is properly positioned within the sleeve. Further, preferentially endpieces 33, 35 are insulated and are adapted to be engaged by contacts 52, 53, respectively, for a purpose described later.

Referring now to other of the components of apparatus 10, heating cabinet 12 is comprised of a housing or oven compartment 12a (e.g. Despatch oven) and bath compartment 22, the lather having been described above. Bath 22 is in communication with and is heated by air from oven 12a which, in turn, is heated by heaters or the like, not shown. An electrical blower (not shown) assures effective hot air circulation between oven 12a and bath 22 through the proper hoses or other conduits, represented by openings 55 in FIG. 1.

Both the oven 12a and bath 22 are equipped with thermocouples (not shown) for temperature monitoring and for maintaining the temperature in the entire system with 1° F. The oven is capable of generating temperatures up to about 250° F. in both the oven and the bath.

Oven 12a also houses recirculating pump system 13 whereby the fluids which are to be pumped through core 20 will be maintained at the simulated temperatures. System 13 delivers continuous and pulse-free fluid flow in either constant-rate, constant-pressure, differential pressure, or recirculating modes and is comprised of positive displacement cylinders 56 and acoustic separator 57. Typically, cylinders 56a, 56c pump water and oil, respectively, to core holder 11 while cylinders 56b, 56d retract water and oil, respectively, through acoustic separator 57. Cylinder 56e is used to control back pressure in the holder 11 by compensating for any variation in the fluid volume which may be caused by the movement of the various cylinders. The drivers for each cylinder is driven by precise stepping motors which are located outside oven 12a and which are controlled by controller 14, 15 which, in turn, are preferably computer-automated.

Acoustic separator 57 (Model AMS900 or CMR NISEP-300. Bergen, Norway) determines the fluid level acoustically and keeps track of the material balance of the fluids to and from core holder 11. Recirculating pump system is highly precise and is preferably similar to the one developed by Quizix SP-6000, Quizix Inc., San Francisco, Calif. and similar to one described as being used for measuring relative permeabilities of a core sample in the paper USE OF A NEW GENERATION RECIRCULATION SYSTEM FOR STEADY-STATE RELATIVE PERMEABILITY MEASUREMENT, Y. Guo and K. O. Vatne, presented at the 7th European IOP Symposium in Moscow, Russia, Oct. 27–29, 1993.

Microwave scanning system 17 is used to determine the water saturation during the measurement of $k_r$, $P_c$, and $R_r$. The microwave absorption technique is based on the microwave energy absorbed by the water molecule dipole in its losing struggle to stay aligned with the oscillating electric field. Measurement of the amount of energy absorbed allows the determination of the water saturation by applying the well known Beer-Lambert absorption law, see "Microwave Attenuation-A New Tool for Monitoring Saturations in Laboratory Flooding experiments", R. W. parson, SPEJ, Aug. 1975; Trans AIME 259, 302–310, which is incorporated herein by reference.

Microwave system 17 is comprised of a mircowave-sending horn or antenna 17a and a receiving horn or antenna 17b which are mounted on the arms of yoke 17c whereby the horns are positioned outside bath 22 on opposite sides of core holder 11. Yoke 17c has a threaded follower nut 17d or the like which cooperates with feed screw 17e which, in turn, is rotated by a micro-stepping motor 17f to thereby move the horns along the longitudinal axis of core holder 11 in a series of precise increments.

Preferably, the microwave system is one which provides absorption over a wide range of frequencies; e.g. 10 MHz-20 GHz having a sweep frequency range with an IF bandwidth of about 10 Hz and a maximum power output of 10 mW thereby making the system relatively safe when compared to other scanning techniques. With an adequate overall dynamic range of 130 dB, the system allows accurate determination of in situ saturation of core 20 (i.e. cylindrical cores having 2" diameters and more). One example of such a microwave system is one marketed by Hewlett-Packer as its Model 8720C. The time domain feature of such a system allows the detection of any microwave beam which might by-pass core 20. Also, reflection and phase angle of the microwave can be measured in addition to the transmission of the signal. Further, unwanted reflection can be filtered out of the main signal.

Calibration, setups, and collected data can be transferred to controlling computer 19 or directly to microwave analyzer 18 (FIG. 1). Proper automated programming allows scanning at several discrete points in a relatively short period of time; e.g. 15 scan locations along a 6 inch long core within 2 minutes. Now that the apparatus 10 and its components have been described in detail, the operation carried out by the apparatus in simultaneously measuring $k_r$, $P_c$, and $R_r$, along with a specific example, is set forth below.

Conductive bands 50 are positioned onto core 20 and patches 31, 32 are positioned, either on core 20 or over ports 29, 30, respectively, after which core 20 (e.g. 2" diameter, 6" long) is placed within sleeve 25 which, in turn, is positioned within core holder 11 between endpieces 33, 35. Once core 20 is in position within core holder 11, simulated reservoir temperatures and pressure may be applied onto the core.

Reservoir temperatures can be simulated by raising the temperature within heating oven 12 to the desired temperature (e.g. 250° F.). Heated air from the oven is then circulated through passages 55 (FIG. 1) into and through bath 22 until all components therein (i.e. core holder 11, core 20, etc.) are heated to the desired temperature. Also, oven the heats pumps 56 and the related fluids to thereby maintain core 20 at the desired temperature during the injecting of fluids.

The absorbent material 26 and all voids within core holder 11 which surround sleeve 25 are filled with an incompressible fluid, e.g. oil. Pressure (simulated reservoir pressure, e.g. up to 5000 psi) is then applied onto the oil into core holder 11 through passage(s) 60 (only one shown in FIG. 3) which, in turn, transmits this pressure onto sleeve 25 and, hence, onto core 20, thereby simulating reservoir pressure in the core 20.

The length of dry core 20 is scanned by microwave system 17 to determine the saturation profile of the core when it is dry. This can be done before or after simulated temperature and pressure are applied to the core. Then, a partial vacuum is drawn on core 20 from the outlet end (i.e. endpiece 33) and water (brine) is injected into the core by pump 56a through inlet end (i.e. endpiece 35). Core 20 is again scanned by microwave system 17 at different time intervals as the core is saturated with water. A typical saturation profile showing the dry core base line and incremental staturation as a function of injected pore volume of an actual core (i.e. Berea sandstone having absolute permeability = 500 md and porosity = 22%) is shown in FIG. 7.

Figure 7:
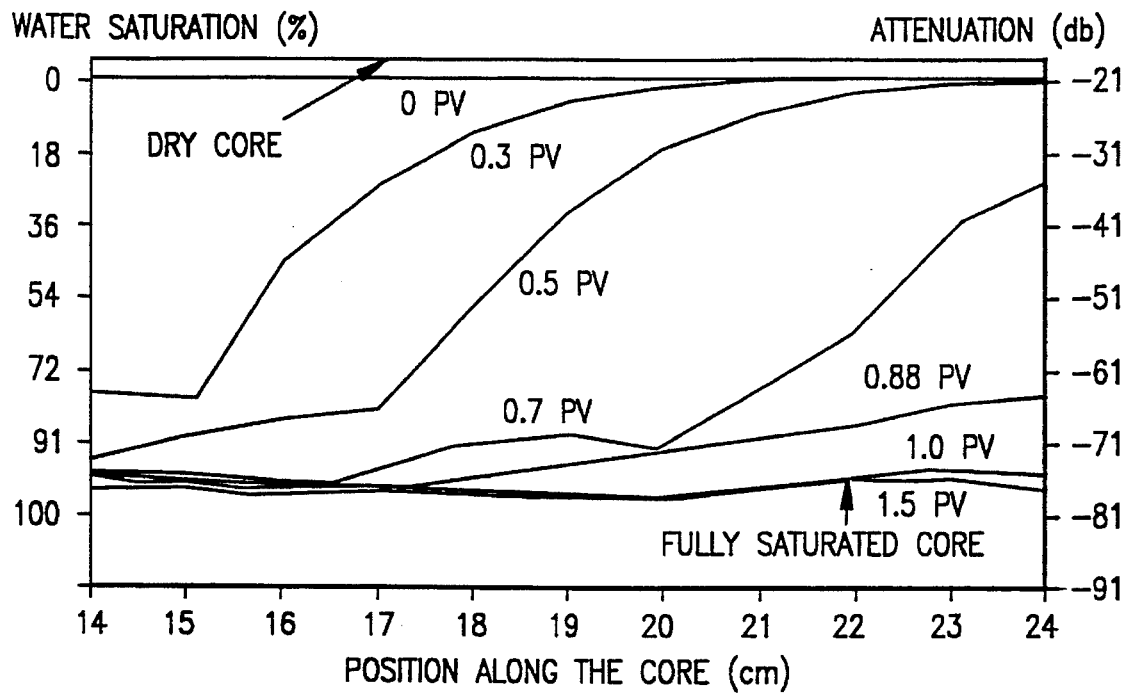
FIG. 7 is a graph correlating both the attenuation of microwave energies and the corresponding water saturation in a core to the position along the core at which the respective measurements were made during the initial saturation of the core with water.

The core used for the data shown in FIG. 7 was scanned at 15 discrete spaced intervals in less than 2 minutes for each pore volume of injected fluid. At each scan location, a microwave signal, e.g. 13 MHz, is transmitted from sending horn 17a (FIG. 2), through the respective microwave transparent material forming the top and bottom of bath 22, through respective windows 24, 26a, and through core 20 where the signal is received by receiving horn 17b.

Energy is absorbed from each microwave signal by any water molecules (relatively unaffected by oil or gas molecules) which may be present in core 20 at that location as the signal passes through the core. Accordingly, the amount by which a signal attenuates is measured and can be used to determine the water saturation at that location by applying the known Beer-Lambert absorption law. For a further discussion of this technique, see "Microwave Attenuation", R. W. Parson, SPE Journal, Aug., 1975; Trans. AIME 259, pps. 302–310.

Once core 20 is fully saturated, the static capillary pressure may be measured by stopping injection of water into core 20 and beginning the injection of oil or gas. The inlet pressure of the injected fluid (i.e. $P_o$) is increased until water begins to flow through porous plate 34 in outlet endpiece 33. $P_o$ is then maintained constant until the flow of water ceases at which time the outlet pressure (i.e. $P_w$) at outlet endpiece 33 is measured. The static capillary pressure is then calculated as $P_o-P_w$.

During the injection of oil or gas, bypass openings 41 in outlet endpiece 33 are closed and oil and/or gas is injected into core 20 by pump 56a through inlet openings 41. If static capillary pressure is measured, after the measurement is made, injection of oil/gas is resumed through inlet endpiece 35 to "desaturate" the core, i.e. establish a desired water saturation in the core, for example, one which approximates or simulates the original water saturation in reservoir from which the core was taken. With the bypass openings 41 in endpiece 33 closed, only water, not oil or gas, can exit core 20 since the only exit is now through water-wet, porous plate 34. By using porous plate 34, lower flow rates can be used in desaturating the core and much lower water saturations can be obtained therein. For example, if plate 34 was not used, saturations of less than 40% would be difficult, if possible at all, to reach in some cases.

Figure 8:
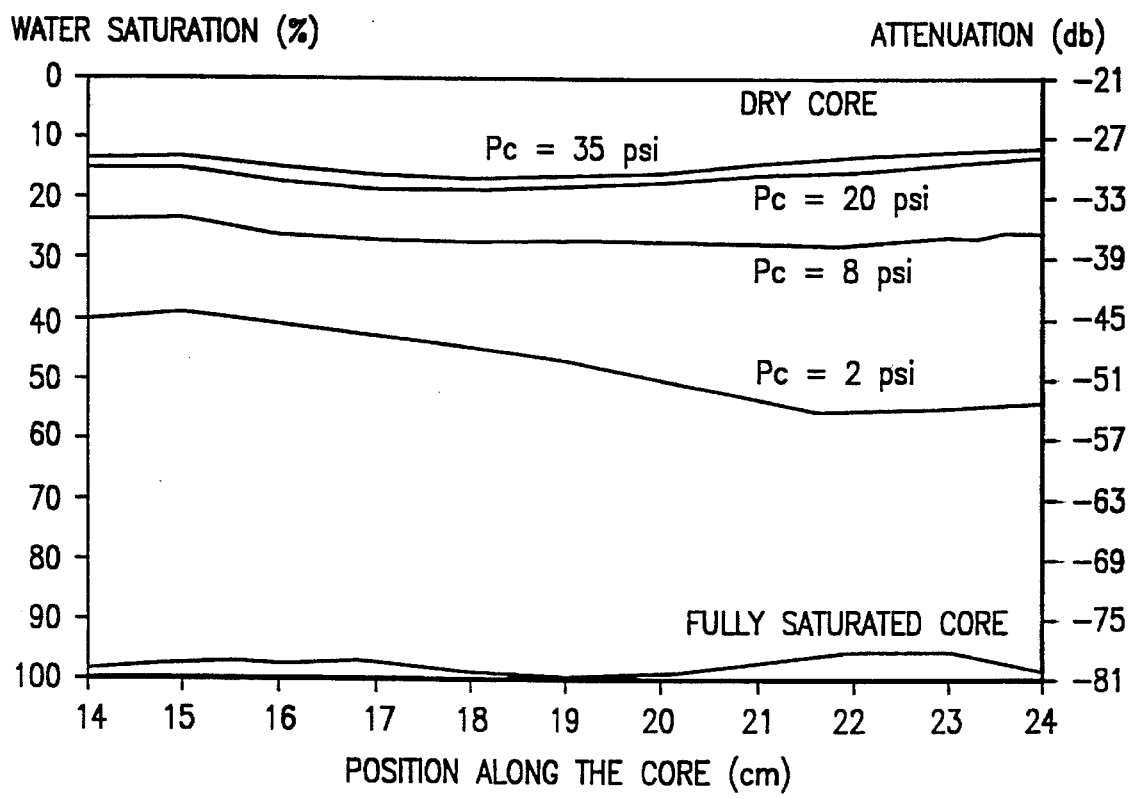
FIG. 8 is a graph correlating both the attenuation of microwave energies and the corresponding water saturation in a core to the position along the core at which the respective measurements were made during reduction of the water saturation in the core.

In the actual core described above, nitrogen gas (acts the same as oil) was injected at a few constant pressure levels to achieve the different water/brine saturations as determined by microwave scanning system 17 and shown in FIG. 8. Residual brine saturation of 18% was achieved in the core of the example at 35 psi capillary pressure within 96 hours with a final residual saturation of 15% was attained at a short time thereafter.

After the desired saturation is achieved in the core, a simulated waterflood operation is carried out during which $k_r$, dynamic $P_c$, and $R_t$ are measured simultaneously. During the simulated waterflood operation, bypass openings 41 in outlet endpiece 33 are opened and water is injected into core 20 by pump 56a through one of inlet openings 41 in inlet endpiece 35. Oil and/or gas is either continuously or periodically injected into core 20 through the other opening 41 in endpiece 35 by pump 56c as a particular operation may dictated.

As will be understood by those skilled in the art, oil and/or gas maybe injected into core 20 during the flooding operation to simulate the flow of oil and/or gas which normally occur from the surrounding reservoir into the path of a waterflood to replace the fluids being displaced during the recovery operation. Again, the core is repeatedly scanned by microwave system 17 as the core is undergoing the simulated waterflood.

Figure 9:
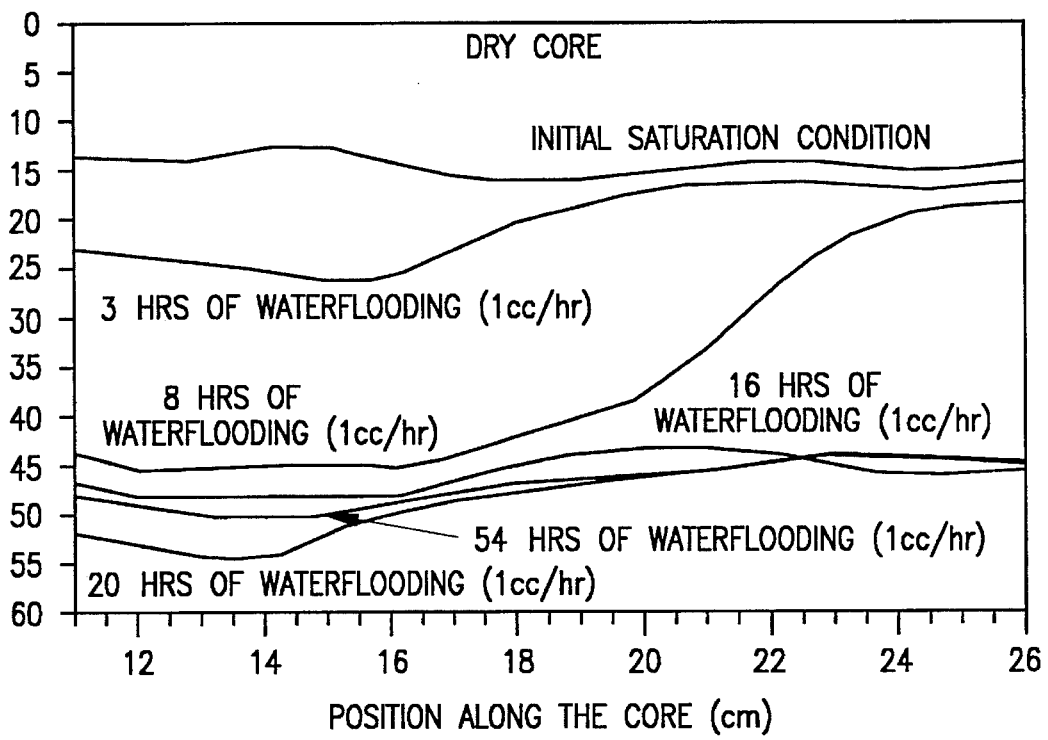
FIG. 9 is a graph correlating a water saturation measurement in a core to the position along the core at which said measurement was made during a simulated waterflood process.
Figure 10:
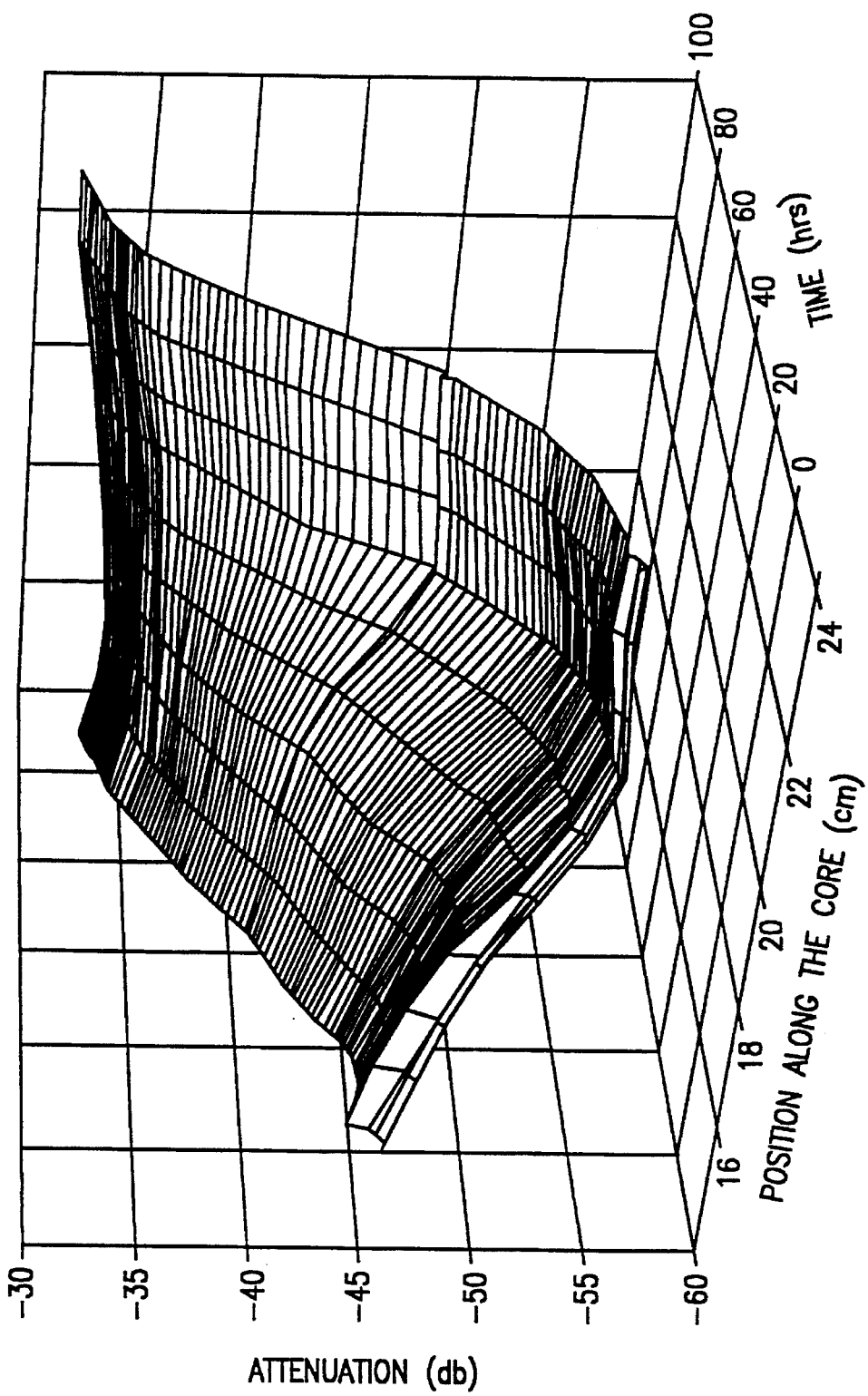
FIG. 10 is a three-axis graph correlating the measurements of attenuation of microwave energies (water saturation) in a core with both the position along the core at which the respective measurements were made and the times of said measurements during a simulated waterflood process.

In the ongoing example, water/brine was injected initially at a rate of 1 cc/hr and a final rate of 2 cc/hr with the resulting saturation profiles shown in FIG. 9. At the rate of 1 cc/hr, the average water saturation increased from 15% to 46% in about 54 hours (1 pore volume of brine injection). The average water saturation further increased from 46% to 48% when the rate was doubled (2 cc/hr). The end-point water relative permeability was measured: $k_{rw}=0.009$ @ $r_{es}$idual gas saturation=52%. FIG. 10 shows a comparison of 100 scans taken in a range of 10% variation in water saturation. All water saturation profiles systematically increased without crossing one another, thus confirming the precision of the apparatus to be within 0.1%.

As set forth above, $k_r$, dynamic $P_c$, and $R_t$ are all measured simultaneously during the simulated waterflood. To measure relative permeability ($k_r$), the pressures within core 20 are measured at the spaced ports 27 and 28. By using known relationships based on the well known "Darcy's equation" the measured differential pressure provides an accurate value for $k_r$ for core 20 for the water saturation existing at the time the measurements were made. For a complete discussion of how differential pressure measurements along a core can be used to calculate $k_r$, see U.S. Pat. No. 4,868,751 to Dogru et al, which is incorporated herein by reference.

To measure dynamic capillary pressure ($P_c$), the pressures of both water and oil are measured through their respective ports 29, 30. As explained above, only water will flow through port 29 while only oil will flow through port 30. Respective transducers (e.g. Model No. 1125-08/G, A52A, distributed by Foxboro, San Jose, Calif.), represented by 66 in FIG. 4 shown, are connected to ports 29, 30, respectively, which allow the respective fluids to enter and leave so that the capillary pressures, $P_w$ and $P_o$ can be measured under equilibrated conditions. The dynamic $P_c$ is equal to $P_o-P_w$.

For a further discussion of dynamic capillary pressures, see "Dynamic Capillary Pressure Curve for Water/Oil Displacement in Porous Media", F. J-M Kalaydjian, SPE 24813, Washington, D.C., Oct. 4–7, 1992; and "A Novel Method for the Determination of Water/oil Capillary Pressures of Mixed Wettability Samples", R. Lenormand et al, 1993 SCA Conference Paper No. 9322.

In measuring electrical resistivity which is extremely useful in interpreting logging data obtained from the actual well which transverses the reservoir from which the core was taken, electrical current is supplied through contact 53 on endpiece 35 in FIG. 4 and which passes longitudinally through core 20 to endpiece 33. Resistivity is measured at points therealong (e.g. spaced contacts 51) while the core 20 is being scanned with system 17 to determine the water saturation at the time the resistivity measurements are being made. For a good discussion of how resistivity measurements relate to the water saturations of a core, see U.S. Pat. Nos. 4,924,187; 4,926,128; 5,093,623; 5,095,273; 5,105, 154; and 5,209,104, all of which are ioncorporated herein by reference.

What is claimed is:

1. An apparatus for obtaining data for simultaneously measuring relative permeability, static and dynamic capillary pressure, and electrical resistivity of a core sample taken from a subterranean reservoir, said apparatus comprising:

a core holder adapted to receive said core sample;

means for applying an elevated temperature to said core sample when said core sample is in said core holder means for applying an elevated pressure to said core sample when said core sample is in said core holder;

means for heating fluids to said elevated temperature;

means for injecting said heated fluids through said core sample when core sample is in said core holder;

means for scanning said core sample at a plurality of points spaced along said core holder while said core sample is in said core holder for determining the water saturation of said core sample at each of said spaced points;

means for measuring the pressure in core sample at points spaced along said core holder;

means for measuring the static capillary pressure of water in said core sample while said core sample is in said core holder;

means for measuring the dynamic capillary pressure of water in said core sample while said core sample is in said core holder;

means for measuring the dynamic capillary pressure of oil and/or gas in said core sample while said core sample is in said core holder; and means for measuring the electrical resistivity of said core sample while said core sample is in said core holder.

2. The apparatus of claim 1 wherein said means for scanning said core sample comprises:

a microwave system comprising:

a sending horn for transmitting microwave signals through said core sample;

a receiving horn for receiving said microwave signals after they have passed through said core sample;

means for positioning said sending horn and said receiving horn on opposite sides of said core holder; and means to move said positioning means to different points along said core holder to thereby position said horns at different points along said core holder.

3. The apparatus of claim 2 including:

an elastic sleeve adapted to snuggly fit around said core sample and adapted to be positioned with said core sample into said core holder.

4. The apparatus of claim 3 wherein said means for measuring pressure at points spaced along said core holder comprises:

a plurality of ports spaced along said elastic sleeve.

5. The apparatus of claim 4 wherein said means for measuring said dynamic capillary pressure of water includes:

a first opening in said sleeve; and means for allowing only water to pass through said first opening;

and wherein said means for measuring said dynamic capillary pressure of oil and/or gas comprises:

a second opening in said sleeve; and means for allowing only oil and gas to pass through said second opening.

6. The apparatus of claim 5 wherein said means for measuring the electrical resistivity comprises:

conductive means in contact with said spaced points on said core sample when said core sample is in said core holder; and means to measure the electric resistivity in said core sample between said conductive means.

7. The apparatus of claim 6 wherein said means for applying said elevated pressure to said core sample includes:

an non-compressible fluid filling said core holder around said sleeve; and means to apply said pressure to said non-compressible fluid within said core holder.

8. An apparatus for obtaining data for simultaneously measuring relative permeability, dynamic capillary pressure, and electrical resistivity of a core sample taken from a subterranean reservoir, said apparatus comprising:

an oven capable of producing high temperatures to simulate the temperature of said subterranean reservoir;

a bath fluidly coupled to said oven whereby heated air from said oven can be circulated through said bath;

a core holder positioned within said bath, said core holder having a body adapted to receive said core sample;

means for applying an elevated pressure to said core sample when said core sample is in said core holder;

means located in said oven for injecting fluids through said core sample when core sample is in said core holder whereby said fluids are heated to said simulated reservoir temperature before the fluids are injected through said core sample;

a microwave scanning system for scanning said core sample at a plurality of spaced points along said core holder while said core sample is in said core holder for determining the water saturation of said core sample at each of said spaced points;

means for measuring the pressure in core sample at points spaced along said core holder;

means for measuring the dynamic capillary pressure of water and oil/gas in said core sample while said core sample is in said core holder;

means for measuring the static capillary pressure of water in said core sample while said core sample is in said core holder; and means for measuring the electrical resistivity of said core sample while said core sample is in said core holder.

9. The apparatus of claim 8 wherein said bath and said body of said core holder are made of microwave transparent material and wherein said microwave system comprises:

a sending horn for transmitting microwave signals through said core sample;

a receiving horn for receiving said microwave signals after they have passed through said core sample;

means for positioning said sending horn and said receiving horn on the outside of said bath whereby they lie on opposite sides of said core holder; and means to move said positioning means to different points along said bath to thereby position said horns at different points along said core holder.

10. The apparatus of claim 9 including:

an elastic sleeve adapted to snuggly fit around said core sample and adapted to be positioned with said core sample into said core holder, said sleeve having diametrically-opposed slots therein which are adapted to align with said microwave horns when said sleeve is in said core holder.

11. The apparatus of claim 10 including:

microwave-absorbent material adapted to be positioned between said sleeve and said body of said core holder when said sleeve and said core sample are in said body of said core holder, said microwave-absorbent material having windows which align with said microwave horns when said sleeve is in position within said core holder.

12. The apparatus of claim 11 wherein said means for measuring pressure at points space along said core holder comprises:

a plurality of ports spaced along said elastic sleeve which are adapted to be connected to pressure transducers.

13. The apparatus of claim 12 wherein said means for measuring said dynamic capillary pressure of water includes:

a first opening in said sleeve; and means for allowing only water to pass through said first opening;

and wherein said means for measuring said dynamic capillary pressure of water-oil comprises:

a second opening in said sleeve; and means for allowing only oil to pass through said second opening.

14. The apparatus of claim 12 wherein said means for measuring the electrical resistivity comprises:

conductive means in contact with said spaced points on said core sample when said core sample is in said core holder; and and means to measure the electric resistivity in said core sample between said conductive means.

15. The apparatus of claim 14 wherein said conductive means comprise:

bands of conductive material positioned around said core sample at spaced point therealong.

16. The apparatus of claim 15 wherein said means for applying said elevated pressure to said core sample includes:

an non-compressible fluid filling said body of said core holder around said sleeve and saturating said microwave-absorbent material; and means to apply said pressure to said non-compressible fluid within said core holder.

17. A method for simultaneously measuring relative permeability, static capillary pressure, dynamic capillary pressure, and electrical resistivity of a core sample taken from a subterranean reservoir, said apparatus comprising:

placing said core sample under elevated temperature and pressure which simulate the original temperature and pressure of the reservoir from which said core sample was taken;

saturating said core sample with water until said core sample is substantially 100% saturated with water;

desaturating said core sample with a hydrocarbon fluid until the residual water saturation is substantially equal to the original water saturation of the reservoir from which the core sample was taken;

flooding said core sample with water to simulate a waterflood;

scanning said core sample with microwave signals at spaced points along said core sample during said saturating, desaturating, and flooding steps to determine the water saturation of said core sample at each of said spaced points at the time a particular scan is made;

measuring the pressure in core sample at points spaced along said core holder during said flooding step;

measuring the dynamic capillary pressure of water-hydrocarbon fluid in said core sample during said flooding step;

measuring the static capillary pressure of said hydrocarbon fluid in said core sample during said flooding step; and measuring the electrical resistivity of said core sample between points spaced along said core sample during said flooding step.

* * * * *